US00PP36478P2

(12) United States Plant Patent
Heuger

(10) Patent No.: US PP36,478 P2
(45) Date of Patent: Feb. 18, 2025

(54) ***HELLEBORUS* PLANT NAMED 'HL 1018'**

(50) Latin Name: ***Helleborus niger* X *Helleborus* x *hybridus***
Varietal Denomination: HL 1018

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 0 days.

(21) Appl. No.: 18/518,354

(22) Filed: Nov. 22, 2023

(51) Int. Cl.
*A01H 5/02* (2018.01)
*A01H 6/72* (2018.01)

(52) U.S. Cl.
USPC ..... Plt./439

(58) Field of Classification Search
USPC ..... Plt./439
CPC ..... A01H 5/02; A01H 5/00; A01H 6/72
See application file for complete search history.

(56) References Cited

PUBLICATIONS

Heuger *Helleborus* retrieved on Sep. 16, 2024 at https://www.heuger.com/en/helleborus/flowering-plants, one page. (Year: 2024).*

* cited by examiner

*Primary Examiner* — June Hwu
(74) *Attorney, Agent, or Firm* — C. Anne Whealy

(57) ABSTRACT

A new and distinct cultivar of *Helleborus* plant named 'HL 1018' characterized by its upright to somewhat outwardly spreading and mounded plant habit; moderately vigorous growth habit; dark green-colored leaflets with lighter green-colored venation; freely flowering habit; white-colored flowers; and good garden performance.

2 Drawing Sheets

Figure 1:
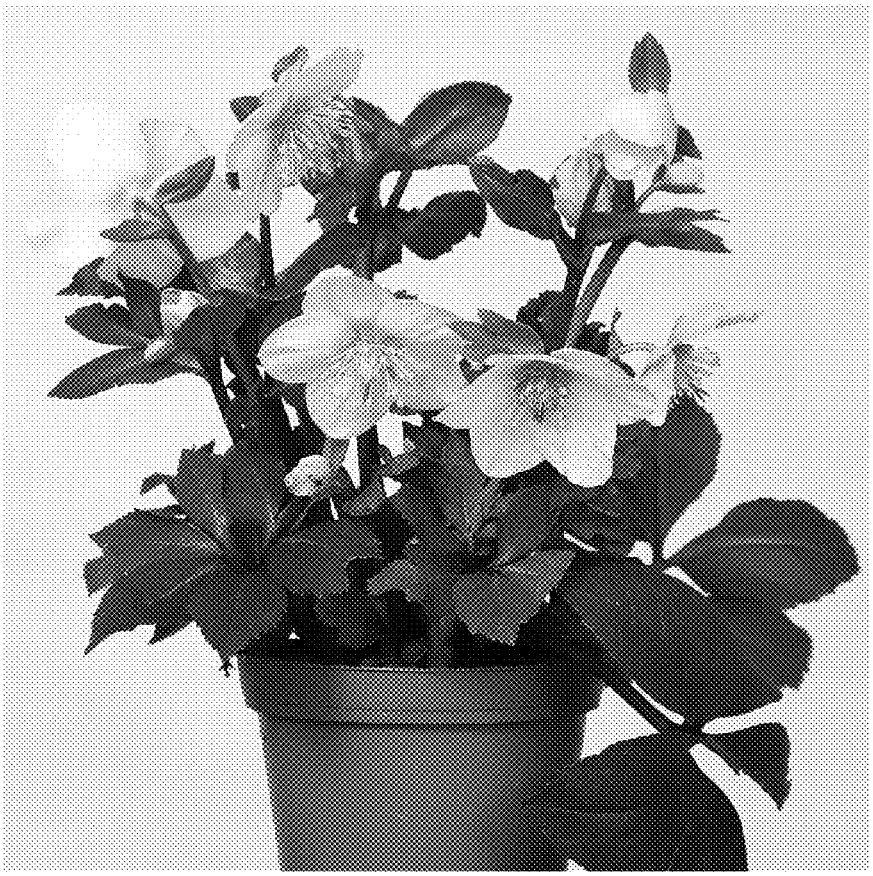

Botanical designation: *Helleborus niger* X *Helleborus* x *hybridus*.

Cultivar denomination: 'HL 1018'.

STATEMENT REGARDING PRIOR DISCLOSURES BY INVENTOR/APPLICANT

An European Community Plant Breeder's Rights application for the instant plant was filed by the Inventor/Applicant, Mr. Josef Heuger of Glandorf, Germany, on Jun. 20, 2023, application number 2023/1374. Foreign priority is not claimed to this application.

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor or Applicant. Inventor/Applicant claims a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Helleborus* plant, botanically known as *Helleborus niger* X *Helleborus* x *hybridus* and hereinafter referred to by the name 'HL 1018'.

The new *Helleborus* plant is a product of a planned breeding program conducted by the Inventor in Glandorf, Germany. The objective of the breeding program was to create new uniform *Helleborus* plants with unique and attractive plant habit, leaf and flower coloration and tolerance to biotic and abiotic stresses.

The new *Helleborus* plant originated from a cross-pollination conducted by the Inventor in Glandorf, Germany in November 2015 of a proprietary selection of *Helleborus niger* identified as code number P1018, not patented, as the female, or seed, parent and a proprietary selection of *Helleborus* x *hybridus* identified as code number O1312, not patented, as the male, or pollen, parent. The new *Helleborus* plant was discovered and selected by the Inventor as a single flowering plant from within the progeny of the stated cross-pollination grown in a controlled greenhouse environment in Glandorf, Germany in December 2015.

Asexual reproduction of the new *Helleborus* plant by in vitro axillary meristem culture in a controlled environment in Glandorf, Germany since April 2016 has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'HL 1018'. These characteristics in combination distinguish 'HL 1018' as a new and distinct *Helleborus* plant:

1. Upright to somewhat outwardly spreading and mounded plant habit.
2. Moderately vigorous growth habit.
3. Dark green-colored leaflets with lighter green-colored venation.
4. Freely flowering habit.

5. White-colored flowers.
6. Good garden performance.

Plants of the new *Helleborus* differ from plants of the female parent selection in the following characteristics:

1. Leaflets of plants of the new *Helleborus* are darker green in color than leaflets of plants of the female parent selection.
2. Flowers of plants of the new *Helleborus* are larger than flowers of plants of the female parent selection.

Plants of the new *Helleborus* differ from plants of the male parent selection in the following characteristics:

1. Leaflets of plants of the new *Helleborus* are darker green in color than leaflets of plants of the male parent selection.
2. Flowers of plants of the new *Helleborus* are whiter in color than flowers of plants of the male parent selection.

Plants of the new *Helleborus* can also be compared to plants of *Helleborus niger* 'COSEH 240', not patented. In side-by-side comparisons, plants of the new *Helleborus* differ primarily from plants of 'COSEH 240' in flower size as plants of the new *Helleborus* have larger flowers than plants of 'COSEH 240'.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet (FIG. 1) is a side perspective view of a typical flowering plant of 'HL 1018' grown in a container.

Figure 2:
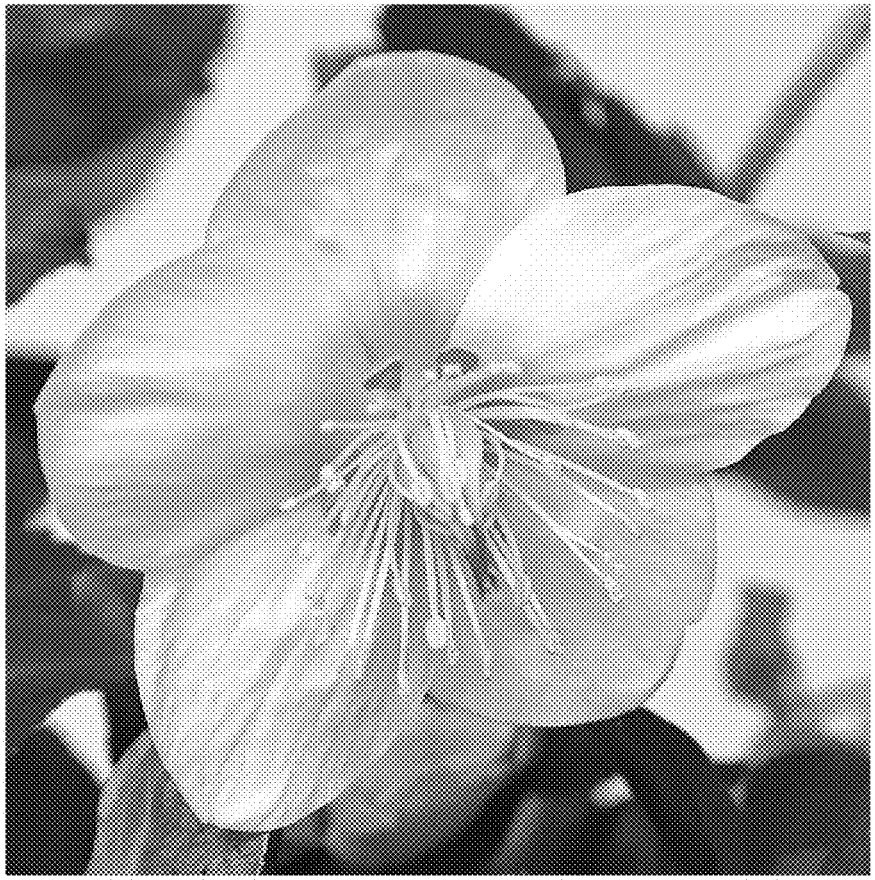

The photograph on the second sheet (FIG. 2) is a close-up view of a typical flower of 'HL 1018'.

DETAILED BOTANICAL DESCRIPTION

The aforementioned photographs and following observations, measurements and values describe plants grown during the winter in 13-cm containers in a glass-covered greenhouse in Glandorf, Germany and under cultural practices typical of commercial *Helleborus* production. During the production of the plants, day temperatures ranged from 12 C to 32 C and night temperatures ranged from 5 C to 12 C. Plants were 48 weeks old when the photographs were taken and 14 months old when the description was taken. In the following description, color references are made to The Royal Horticultural Society Colour Chart, 2015 Edition, except where general terms of ordinary dictionary significance are used.

Botanical classification: *Helleborus niger* X *Helleborus* x *hybridus* 'HL 1018'.

Parentage:

*Female, or seed, parent*.—Proprietary selection of *Helleborus niger* identified as code number P1018, not patented.

*Male, or pollen, parent*.—Proprietary selection of *Helleborus* x *hybridus* identified as code number O1312, not patented.

Propagation:

*Type*.—In vitro axillary meristem culture.

*Time to initiate roots, winter*.—About 55 days at temperatures about 12 C.

*Time to produce a rooted young plant, winter*.—About 170 days at temperatures ranging from about 4 C to 15 C.

*Root description*.—Thick to thin, fleshy; typically white to brownish in color, actual color of the roots is dependent on substrate composition, water quality, fertilizer type and formulation, substrate temperature and physiological age of roots.

*Rooting habit*.—Low branching; sparse.

Plant description:

*Plant and growth habit*.—Herbaceous perennial; upright to somewhat outwardly spreading and mounding plant habit with flowers held slightly above to well above the foliar plane; plant shape, flattened globular; moderately vigorous growth habit and moderate growth rate.

*Plant height, soil level to top of foliar plane*.—About 14.5 cm.

*Plant height, soil level to top of flowers*.—About 23.9 cm.

*Plant diameter* (*area of spread*).—About 30.3 cm.

Leaf description:

*Arrangement*.—Leaves arranged in a basal rosette; leaves palmately compound with typically five leaflets per leaf.

*Leaf length*.—About 12.7 cm.

*Leaf width*.—About 14.9 cm.

*Leaflet length*.—About 8.6 cm.

*Leaflet width*.—About 5.6 cm.

*Leaf shape*.—Palmate; roughly reniform in outline.

*Leaflet shape*.—Elliptic to obovate.

*Leaflet apex*.—Acute.

*Leaflet base*.—Attenuate.

*Leaflet margin*.—Serrate; slightly coarsely undulate.

*Leaflet texture and luster, upper and lower surfaces*.—Smooth, glabrous; coriaceous and tough; slightly glossy.

*Leaflet venation pattern*.—Pinnate and reticulate.

*Leaflet color*.—Developing leaflets, upper surface: Close to 137A; at the base, close to N186C. Developing leaflets, lower surface: Close to a blend of 138A and 147B; midvein, close to 183A and 183B. Fully developed leaflets, upper surface: Slightly darker than a blend of NN137A and 147A; at the base, tinged with close to N186A; venation, close to 144A. Fully developed leaflets, lower surface: Close to 147B; venation, close to 199A.

*Petioles*.—Length: About 9.8 cm. Diameter: About 6 mm by 7 mm. Strength: Strong. Texture and luster, upper and lower surfaces: Smooth, glabrous; slightly glossy. Color, upper and lower surfaces: Close to 146C; moderately to heavily covered with fine dots, close to N186C.

Flower description:

*Flower shape and habit*.—Single rotate bowl-shaped flowers arranged in panicles; freely flowering habit with about two to five flowers per inflorescence and about 20 flowers and flower buds per plant; flowers face mostly outwardly to slightly nodding.

*Fragrance*.—None detected.

*Natural flowering season*.—Plants begin flowering about ten months after planting; plants flower naturally from early winter to late winter in Germany.

*Flower longevity on the plant*.—About ten days; sepals persistent, other flower parts are not persistent.

*Flower buds*.—Length: About 2.3 cm. Diameter: About 1.5 cm. Shape: Ovate. Texture and luster: Smooth, glabrous; slightly glossy. Color: Close to 157C; towards the base, close to 145B to 145C.

*Inflorescence height* (*including peduncle*).—About 22.4 cm.

*Inflorescence diameter*.—About 11.9 cm.

*Flower diameter*.—About 7.3 cm.

*Flower depth*.—About 2.5 cm.

*Petals*.—All petals are transformed into nectaries.

*Sepals*.—Quantity and arrangement: About five, occasionally, six, arranged in a single whorl. Length: About 3.7 cm. Width: About 3.2 cm. Shape: Broadly ovate; slightly concave. Apex: Broadly and bluntly acute to narrowly obtuse. Base: Cuneate. Margin: Entire; not undulate. Texture and luster, upper and lower surfaces: Smooth, glabrous; slightly glossy. Color: When opening, upper surface: Close to NN155B; at the base, close to 145C. When opening, lower surface: Close to 155C; at the base, close to 145B to 145C. Fully opened, upper surface: Close to NN155C; at the base, close to 145A to 145B; venation, similar to lamina colors; color does not change with subsequent development. Fully opened, lower surface: Close to NN155B to NN155C; at the base, close to 145A to 145B; venation, similar to lamina colors; color does not change with subsequent development.

*Flower bracts*.—Quantity per flower: Typically one or two. Length: About 5.3 cm. Width: About 4.1 cm. Shape: Ovate to obovate. Apex: Acute to three-lobed. Base: Truncate to cuneate. Margin: Mostly entire; distally, occasionally, shallowly serrate; coarsely undulate. Color, upper surface: Slightly darker than a blend of NN137A and 147A; towards the base, close to 145A to 145B; midvein, occasionally tinged with close to 187A and 187B. Color, lower surface: Close to 147B; midvein, tinged with close to 187A and 187B.

*Peduncles*.—Length: About 17 cm. Diameter: About 7 mm to 8.5 mm. Aspect: About 15 degrees from vertical. Strength: Strong. Texture and luster: Smooth, glabrous; moderately glossy. Color: Close to 146D; heavily covered with fine dots, close to 183A to 183B.

*Pedicels*.—Length: About 2.8 cm. Diameter: About 3 mm. Aspect: About 15 degrees from peduncle axis. Strength: Moderately strong. Texture and luster: Smooth, glabrous; slightly to moderately glossy. Color: Close to 145A and 145B; slightly to moderately covered with fine dots, close to 182B and 182C.

*Reproductive organs*.—Stamens: Quantity per flower: Up to 100.Filament length: About 1.7 cm. Filament color: Close to 157D. Anther shape: Double and broadly reniform; basifixed. Anther size: About 2 mm by 3 mm. Anther color: Close to 154C to 154D. Pollen amount: Sparse to moderate. Pollen color: Close to 4D to lighter than 4D. Pistils: Quantity per flower: About five or six. Pistil length: About 1.1 cm. Stigma diameter: About 0.3 mm. Stigma shape: Club-shaped. Stigma color: Close to 156D. Style length: About 1.05 cm. Style color: Close to 186C. Ovary color: Close to 145C. Nectaries (transformed petals): Quantity per flower: About nine to twelve. Length: About 1 cm. Diameter: About 5 mm. Shape: Tubular, flattened; apices, obtuse. Texture and luster, inner and outer surfaces: Smooth, glabrous; slightly glossy. Color, immature, inner and outer surfaces: Close to 144B. Color, mature, inner and outer surfaces: Close to a blend of 144A and 144B; towards the apex, close to N144C; venation, similar to lamina colors; color does not change with subsequent development. Seeds and fruits: To date, seed and fruit development have not been observed on plants of the new *Helleborus*.

Garden performance: Plants of the new *Helleborus* have been observed to have good garden performance and to tolerate rain, wind, high temperatures about 35 C and to be suitable for USDA Hardiness Zones 5 through 9.

Pathogen & pest resistance: To date, plants of the new *Helleborus* have not been observed to be resistant to pathogens and pests common to *Helleborus* plants.

It is claimed:

1. A new and distinct *Helleborus* plant named 'HL 1018' as illustrated and described.

* * * * *